US006992072B2

(12) United States Patent
Walker

(10) Patent No.: US 6,992,072 B2
(45) Date of Patent: Jan. 31, 2006

(54) COMBATING SIDE-EFFECTS

(75) Inventor: Ulrich Walker, Freiburg (DE)

(73) Assignee: Pharma Nord ApS, Vojens (DK)

( * ) Notice: Subject to any disclaimer, the term of this patent is extended or adjusted under 35 U.S.C. 154(b) by 40 days.

(21) Appl. No.: 10/468,846

(22) PCT Filed: Feb. 27, 2002

(86) PCT No.: PCT/DE02/00721

§ 371 (c)(1),
(2), (4) Date: Feb. 11, 2004

(87) PCT Pub. No.: WO02/069943

PCT Pub. Date: Sep. 12, 2002

(65) Prior Publication Data

US 2004/0138157 A1    Jul. 15, 2004

(30) Foreign Application Priority Data

Mar. 3, 2001    (DE) ................. 101 10 355

(51) Int. Cl.
*A61K 31/7052* (2006.01)
*A61K 31/7068* (2006.01)
*A61K 31/7072* (2006.01)
*A61K 31/70* (2006.01)

(52) U.S. Cl. ............................ 514/49; 514/50; 514/43; 514/42; 536/28.5

(58) Field of Classification Search ............... 514/49, 514/43, 42, 50; 536/28.5
See application file for complete search history.

(56) References Cited

U.S. PATENT DOCUMENTS 5,141,943 A    8/1992    Naguib et al.
5,567,689 A    10/1996   Sommadossi et al.

FOREIGN PATENT DOCUMENTS

| DD | 114 411 A | 8/1975 |
| WO | 93 01202 | 1/1993 |
| WO | WO 93-01202 | * 1/1993 |
| WO | 93 12128 | 6/1993 |
| WO | 00 11952 | 3/2000 |
| WO | 00 50043 | 8/2000 |

OTHER PUBLICATIONS

Martinez et al., Clinical infectious disease: an official publication of the Infectious Disease Society of America, (Nov. 2000) 31 (5) 1266-73. Electronic Publication: Nov. 6, 2000) (Abstract Sent).*
U.A. Walker, et al., "Evidence of Nucleoside Analogue Reverse Transcriptase Inhibitor-Associated Genetic and Structural Defects of Mitochondria in Adipose Tissue of HIV-Infected Patients", JAIDS, Journal of Acquired Immune Deficiency Syndromes, vol. 29, No. 2, Feb. 1, 2002, pp. 117-121.
J. Amin, et al., "Combined Analysis of Two-Year Follow-Up From Two Open-Label Randomized Trials Comparing Efficacy of Three Nucleoside Reverse Transcriptase Inhibitor Backbones for Previously Untreated HIV-1 Infection: Ozcombo 1 and 2", HIV Clin Trials, 4(4), 2003, pp. 252-261.
G.Chene, et al., "Role of Long-Term Nucleoside-Analogue Therapy in Lipodystrophy and Metabolic Disorders in Human Immunodeficiency Virus-Infected Patients", CID, 34, Mar. 1, 2002, pp. 649-657.
V. Joly, et al., "Increased Risk of Lipoatrophy Under Stavudine in HIV-1 Infected Patients: Results of a Substudy from a Comparative Trial", AIDS, vol. 16, No. 18, 2002, pp. 2447-2454.
A. Martin, et al., "Reversibility of Lipoatrophy in HIV-Infected Patients 2 Years After Switching From a Thymidine Analogue to Abacavir: The Mitox Extension Study", AIDS, vol. 18, No. 7, 2004, pp. 1029-1036.
G.A. McComsey, et al., "Improvements in Lipoatrophy, Mitochondrial DNA Levels and Fat Apoptosis After Replacing Stavudine with Abacavir or Zidovudine", AIDS, vol. 19, No. 1, 2005, pp. 15-23.

(Continued)

*Primary Examiner*—Samuel Barts
*Assistant Examiner*—Michael C. Henry
(74) *Attorney, Agent, or Firm*—Oblon, Spivak, McClelland, Maier & Neustadt, P.C.

(57) ABSTRACT

The invention relates to the use of active ingredients, which increase the concentration of pyrimidine-based elements for nucleic acid biosynthesis in the body, in particular to the use of pyrimidine nucleosides and/or prodrugs produced therefrom, for reducing the side-effects of inhibitors of nucleic acid biosynthesis or their precursors, in particular by activating the biosynthesis of mitochondrial DNA (mtDNA). The invention also relates to the use of said active ingredients, in particular pyrimidine nucleosides and/or prodrugs for producing pharmaceutical preparations for reducing the aforementioned side-effects and to combinations or products for administering active ingredients of this type, in particular pyrimidine nucleosides and/or prodrugs produced therefrom, comprising inhibitors of nucleic acid biosynthesis or their precursors. The invention further relates to methods for treating the side-effects of inhibitors of nucleic acid biosynthesis or their precursors using the aforementioned active ingredients, in particular pyrimidine nucleosides and/or prodrugs produced therefrom, or the aforementioned combinations or products and to corresponding pharmaceutical preparations. Side-effects of HAART (Highly Active Anti-Retroviral Therapy) and side-effects of other anti-viral nucleoside analogous agents, which inhibit the mitochondrial γ-polymerases, can in particular be prophylactically and/or therapeutically treated in this manner.

7 Claims, No Drawings

OTHER PUBLICATIONS

C.L. Cherry, et al., "Increased Adipocyte Apoptosis in Lipoatrophy Improves within 48 Weeks of Switching Patient Therapy from Stavudine to Abacavir or Zidovudine", J Acquir Immune Defic Syndr, vol. 38, No. 3, Mar. 1, 2005, pp. 263-267.

U.A. Walker, et al., "Uridine Abrogates the Adverse Effects of Pyrimidine Analogues on Adipose Cell Functions", Antiviral Therapy, 9, 2004, w/attached manuscript pp. 1-26.

C.J. Van Groeningen, et al., "Clinical and Pharmacokinetic Studies of Prolonged Administration of High-Dose Uridine Intended for Rescue from 5-Fu Toxicity", Cancer Treatment Reports, vol. 70, No. 6, Jun. 1986, pp. 745-750.

A. Leyva, et al., "Phase I and Pharmacokinetic Studies of High-Dose Uridine Intended for Rescue from 5-Fluorouracil Toxicity", Cancer Research, vol. 44, Dec. 1984, pp. 5928-5933.

C.J. Van Groeningen, et al., "Reversal of 5-Fluorouracil-Induced Toxicity by Oral Administration of Uridine", Annals of Oncology, vol. 4, 1993, pp. 317-320.

C.J. Van Groeningen, et al., "Phase I Clinical and Pharmacokinetics Study of Orally Administered Uridine", Proceedings of the AACR, vol. 28, Mar. 1987, p. 195.

D.P. Kelsen, et al., "Phase I Trial of PN401, an Oral Prodrug of Uridine to Prevent Toxicity from Fluorouracil in Patients with Advanced Cancer", Journal of Clinical Oncology, vol. 15, No. 4, Apr. 1997, pp. 1511-1517.

M. Hidalgo, et al., "Phase I and Pharmacologic Study of PN401 and Fluorouracil in Patients with Advanced Solid Malignancies", Journal of Clinical Oncology, vol. 18, No. 1, Jan. 2000, pp. 167-177.

T.N. Kakuda, et al., "Pharmacology of Nucleoside and Nucleotide Reverse Transcriptase Inhibitor-Induced Mitochondrial Toxicity", Clinical Therapeurtics, vol. 22, No. 6, pp. 685-708, Jun. 2000.

O.M. Ashour, et al., "Modulation of 5-Fluorouracil Host Toxicity by 5-(Benzyloxybenzyl)Barbituric Acid Acyclonucleoside, A Uridine Phosphorylase Inhibitor, and 2',3',5'-Tri-0-Acetaluridine, a Prodrug of Uridine", Biochemical Pharmacology, vol. 60, No. 3, pp. 427-431, 2000.

* cited by examiner

COMBATING SIDE-EFFECTS

The invention relates to the use of active agents that raise the concentration of pyrimidine-base building blocks for the biosynthesis of nucleic acids in the body, specifically of pyrimidine nucleosides and/or prodrugs of them, for the reduction of side effects of inhibitors of the biosynthesis of nucleic acids or their preliminary stages, specifically through activation of biosynthesis of mitochondrial DNA (mtDNA), the use of these active agents, specifically of pyrimidine nucleosides and/or prodrugs, for the manufacture of pharmaceutical preparations for the reduction of the named side effects, combinations or products for the administration of such agents, specifically, of pyrimidine nucleosides and/or prodrugs of them, with inhibitors of the biosynthesis of nucleic acids or their precursors, methods for the treatment of side effects of inhibitors of the biosynthesis of nucleic acids or their precursors, using the named active agents, specifically pyrimidine nucleosides and/or prodrugs of them, or the named combinations or products, and corresponding pharmaceutical preparations.

BACKGROUND OF THE INVENTION

The term "HAART" (Highly Active Anti-Retroviral Therapy) summarizes a series of methods of treatment, in connection with which anti-retroviral chemotherapeutic substances, specifically inhibiting substances of Reverse Transcriptase (RT) and inhibiting substances of HIV protease are administered in combination to combat AIDS. Typical treatment regimens employ two nucleoside analogue RT inhibitors (NRTI's) and an HIV protease inhibitor or a non-nucleoside analogue RT inhibitor. After bone marrow suppression and the accompanying negative effects of some reverse transcriptase inhibitors on the differential blood count and the immune defense were established as side effects, in part along with neuropathies and myopathies (also of the heart muscle), further side effects became evident with the new forms of therapy. One of them is the so-called lipodystrophy. This term covers a series of symptoms and side effects. While high cholesterol and triglyceride levels are often found with protease inhibitors, further side effects have been observed with the so-called nucleoside analogue, reverse-transcriptase inhibitors (NRTI's). Particularly noticeable are the physical changes, such as the disappearance of subcutaneous fatty tissue in the face, which can lead to shrunken cheeks and sunken eye sockets. The subcutaneous fatty tissue can also be reduced in other parts of the body (e.g., the extremities). In part simultaneously with this, but also in isolation, an abnormal increase in fatty tissue may occur (e.g., in the breasts of the woman and man, intra-abdominally, and in the neck and on the back of the neck). In particular, the latter symptoms are a burden for the patients, who suffer under the fact that, as a result of the therapy, people can "see the disease." Possible consequences of the changes in fat are, among other things, changes in the metabolism in other metabolic system areas, e.g., in the glycohomeostasis through resistance to insulin, and changes in the fat metabolism, and with that, e.g., the composition of the blood lipids. All of these changes are comprised in the term lipodystrophy. A further effect, especially of the NRTI's, consists in damage to the liver, especially in the direction of an increase in fat (micro- or macro-vesicular steatosis, steato-hepatitis, up to and including liver failure). In addition, numerous other syndromes appear, such as changes in spermatogenesis (reduced sperm count, reduced sperm quality, specifically reduced sperm motility), a surge in cases of pancreatitis and a syndrome of osteopenia, which can be associated with an increase in the lactate level. Further, disorders of the kidney tubuli have been observed, e.g., reduced phosphate resorption. Finally, numerous HIV patients taking NRTI in long-term anti-retroviral therapy manifest diminished aerobic capacity on the basis of a diminished oxygen intake. All of the above-named changes seem to be long-term side effects of the different active agents used in the context of HAART, in connection with which most of the above-named problems seem to be those of long-term therapy with NRTI's.

Because HAART makes available very effective therapies, however, there is a great need for forms of treatment of this nature. For this reason, options are urgently needed to limit, reduce, or eliminate these new side effects, specifically lipodystrophy, disorders of spermatogenesis and the sperm function, the imbalance in the mineral salt content of the bones (above and below referred to as osteopenia), the more frequent appearance of pancreatitis, diminished aerobic capacity and/or disorders of the kidney functions, as well as myopathies and/or weakening of the cells of the immune system. Up to this time, primarily adjustments in nutrition and prophylaxis against side effects were used as therapy, in addition to the intake of vitamins and minerals and the intake of unsaturated fatty acids, carnitine and the glutathion precursor N-acetylcysteine, without a noticeable effect.

A further side effect of NRTI's is hyperlacticemia, which can lead to lactic acidosis, with symptomatic and in part life-threatening acute forms. Discontinuing the NRTI's only leads slowly to recovery, and the use of cofactors or antioxidants such as ubiquinone, antioxidants, carnitine, riboflavin, and thiamin, has only a limited effect.

The treatment of all the side effects named has, all in all, been rather unsatisfactory up to now the temporary discontinuance of NRTI's and/or other inhibitors of the biosynthesis of nucleic acids or its precursors, because of the danger of the development of resistance and progression of HIV-associated immune deficiency, is for the most part undesirable, as is a change in medication.

Patients infected with other viruses, e.g., the hepatitis B virus, the hepatitis C virus, the CMV virus, other herpes viruses (e.g., the varizella-zoster virus, and herpes simplex viruses, the Epstein-Barr virus, HHV type 6 and HHV type 8) and by the JC-virus, can also be treated with nucleoside analogues (e.g., with Acyclovir, Valacyclovir, Famaciclovir, Brivudin, Ribavirin, Ganciclovir, Tenofovir, Cidofovir and Adefovir) and suffer the same above-mentioned side effects. Conversely, the simultaneous therapy with the nucleoside analogues against above-mentioned viruses can intensify the long-term side effects of the above-mentioned anti-HIV drugs. Individual side effects in the use of these antiviral substances can be significantly more evident than those with NRTI's, e.g., manifestation of the disorder of the kidney known as Fanconi syndrome.

For this reason, there is an urgent need to combat the above-named undesirable effects of these medications, specifically lipodystrophy, changes in the sperm and/or osteopenia, in addition, pancreatitis, disorder of the kidney, diminished aerobic endurance, liver damage and/or lactic acidosis, as well as to combat myopathies and to reactivate existing immune cells.

In U.S. Pat. No. 5,968,914, the treatment of bone marrow suppression induced by AZT and the accompanying anemia, as well as ddC-induced peripheral neuropathy, ulcers of the mouth, reduced number of thrombocytes, and the side effects on the muscles, peripheral nervous system, immune system, and gastro-intestinal tract caused by anti-viral therapy through the administration of acylated non-methylated pyridine nucleoside, is described. WO 00/11952 describes, among other things, the treatment of the side effects of cancer chemotherapy, such as peripheral neuropathies, kidney ailments and fatigue caused by the administration of pyrimidine nucleotide precursors.

GENERAL DESCRIPTION OF THE INVENTION

It has been established that a large number of the side effects of NRTI's and of the above-listed other nucleoside analogue anti-viral medications, specifically lipodystrophy, changes in the sperm and/or osteopenia, in addition, liver damage (specifically steato-hepatitis), hyperlacticemia/lactic acidosis, pancreatitis, disorders of kidney function and/or diminished aerobic endurance and/or in addition, weakening of the existing cells of the immune system, can be effectively treated with active agents, preferably pyrimidine nucleosides and/or the prodrugs of them, that increase the concentration of pyrimidine bases for the synthesis of nucleic acids in the body.

Without intending to exclude other effective means and mechanisms by this statement, the effect can be plausibly explained in the following way: NRTI's inhibit the gamma-polymerase required for mitochondria) DNA-replication, and thereby the synthesis of mitochondria) respiratory chain subunits. This inhibition is based, on the one hand, on the competition of the NRTI's with the natural mitochondrial nucleotides and, on the other hand, on the fact that the NRTI's serve as substrates for the polymerase, and because they lack a 3-beta-hydroxy group, they cause chain termination. The resulting reduction of the quantity of mitochondrial DNA (mtDNA) then leads to a reduced synthesis of these subunits of the mitochondrial respiratory chain, which are encoded by the mtDNA. This leads to the diminishing of the activity of the dihydro-orotate dehydrogenase (DHODH), an enzyme that is involved with the de novo synthesis of pyrimidine nucleotides. The reason is that the activity of the DHODH is coupled to the activity of the respiratory chain: the synthesis of orotate, a preliminary stage for pyrimidine nucleotides, is only possible if electrons can be transferred from dihydroorotate to ubiquinone (coenzyme Q). This goes on continuously only if respiratory chain complexes III and IV are functional. Orotate is then normally transformed into uridine monophosphate, from which all of the other pyrimidines are biosynthesized. For this reason, it can be assumed that the inhibition of the function of the respiratory chain as a result of the presence of NRTI's and/or other anti-viral nucleoside analogues, which target other viruses, leads to a reduction of the intramitrochondrial pyrimidine nucleosides and nucleotides. In consequence of this, the NRTI concentration increases relative to that of the pyrimidine nucleotides; what results is an intensified interaction with the gamma-polymerase. A vicious circle arises, which leads by virtue of a further reduction of the mtDNA to even less pyrimidine nucleotide synthesis, etc. The effect of the administration of the active agents described above and below, according to the invention, specifically pyrimidine nucleosides and/or prodrugs of them, breaks this vicious circle by making available an exogenous source of these building blocks for mtDNA. In this way, it successfully reduces the side effects of the nucleoside analogues and other substances inhibiting the biosynthesis of mitochondrial nucleic acids, specifically mtDNA, or where relevant, their precursors, and specifically combats the long-term effects described above.

The invention, therefore, is based on the use of active agents that increase the concentration of pyrimidine base building blocks for the synthesis of nucleic acids in the body, specifically of pyrimidine nucleosides and/or their derivates, in order to eliminate the undesirable side effects of inhibitors of the biosynthesis of nucleic acids or their precursors, specifically on the use of pyrimidine nucleosides and/or their derivates for (complete or partial) compensation for the depletion of mtDNA caused by these inhibitors, specifically by NRTI's and/or other anti-viral nucleoside analogues, and the accompanying side effects.

DETAILED DESCRIPTION OF THE INVENTION

The invention involves (i) the use of active agents that increase the concentration of pyrimidine base building blocks for the biosynthesis of nucleic acids in the body, specifically pyrimidine nucleosides and/or prodrugs of them, for the reduction of side effects of inhibitors of the biosynthesis of nucleic acids or their precursors, specifically of NRTI's and/or of other anti-viral nucleoside analogues, specifically the use of pyrimidine nucleosides and/or their prodrugs for the activation of the biosynthesis of mitochondria) DNA (mtDNA), i.e., for the (complete or partial) compensation for depletion of mtDNA (which is specifically based on the inhibition of mitochondrial gamma-polymerase) and is caused by these inhibitors, specifically NRTI's and/or other anti-viral nucleoside analogues, and of the accompanying side effects, primarily lipodystrophy, changes in the sperm and/or osteopenia, in addition, liver damage (primarily micro- or macro-vesicular steatosis, steato-hepatitis, up to and including liver failure), hyperlacticemia/lactic acidosis, pancreatitis, disorder of the kidney function, diminished aerobic endurance and/or inhibition of the activity of existing immune cells; (ii) the use of these active agents, specifically pyrimidine nucleosides and/or prodrugs, for the manufacture of pharmaceutical preparations for the reduction the named side effects, specifically through activation of the biosynthesis of mitochondrial DNA (mtDNA); (iii) combinations of preparations or products for the administration of such agents, specifically pyrimidine nucleosides and/or the prodrugs of them, with inhibitors of the biosynthesis of nucleic acids or their precursors; (iv) methods for the treatment of side effects of inhibitors of the biosynthesis of nucleic acids or their precursors, specifically through the activation of biosynthesis of mitochondrial DNA (mtDNA), using the named active agents, specifically pyrimidine nucleosides and/or prodrugs of them, or the named combinations or products; and (v) corresponding pharmaceutical preparations.

The general concepts and symbols above and below preferably have the meanings listed below, provided that nothing is stated to the contrary. Insofar as the general concepts and symbols named above and below are used, these can be replaced independently of one another by the more specific definitions, which results in preferred embodiments of the invention.

The invention can be used prophylactically (i.e., for complete or at least partial avoidance of the named side effects or parallel to a treatment with inhibitors of biosynthesis of nucleic acids or their precursors, for example HAART, and/or in the context of therapy for other viral infections), and/or in case side effects have already appeared, it can be used therapeutically (for example parallel to a therapy with the named inhibiting substances, or in treatment-free periods of time, e.g., (specifically in the case of treatment for lactic acidosis and/or hepato-toxicity) after the discontinuation of the inhibiting substances; all this is encompassed in the present invention. In a preferred embodiment of the invention, active agents according to the present invention may also be used for treatment, i.e., prevention and therapy, of the named side effects (specifically, insofar as they apply to the mitachondriopathies caused by the anti-viral therapy), in the fetus and after birth, particularly in the first year of life (e.g., in the case of newborns), in the context of the perinatal transmission prophylaxis with inhibitors of the biosynthesis of nucleic acids or their precursors.

Active agents that increase the concentration of pyrimidine building blocks for the biosynthesis of nucleic acids in the body are, in the first place, compounds which, under physiological conditions, have the capacity to overcome an inhibition of the biosynthesis of mitochondria) DNA (mtDNA) completely or at least partially (compensation and/or activation), if by treatment with inhibitors of biosynthesis of nucleic acids or their precursors, specifically NRTI's and/or other anti-viral nucleoside analogues, this synthesis can be completely or partially prevented (i.e., specifically prophylactically before, prophylactically or therapeutically during, and/or therapeutically after an appropriate corresponding anti-viral treatment), specifically by the inhibition of dihydro-orotate dehydrogenase (DHODH). Among the active agents are specifically those compounds that have the capacity to increase the concentration of orotic acid, ribonucleosides, deoxyribonucleosides, ribonucleotides and/or deoxyribonucleotides, primarily uridine and, in addition, cytidine, in the body, specifically in the blood plasma, cells or their organelles such as mitochondria, a situation which, as described above, makes possible an activation or reactivation of the synthesis of mtDNA. Included here are specifically compounds like uridine-phosphorylase inhibitors, inhibitors of uridine secretion, compounds that compete with uridine in renal transport mechanisms, or pyrimidine nucleosides and/or prodrugs of them. It is also possible to combine two or more of the active agents named above and below, be it in a fixed combination, or staggered over a period of time.

Compounds that are regarded as uridine phosphorylase inhibitors are, specifically, compounds such as 5-benzylbarbiturate derivates, 5-benzylbarbiturate, 5-benzyloxybenzyl-barbiturate, 5-benzyloxybenzyl- or 5-benzyloxybenzylacetyl-1-[(1-hydroxy-2-ethoxy)methyl]barbiturate, 5-benzyloxybenzyl-1-[(1,3-dihydroxy-2-propoxy)methyl]barbiturate, 5-benzyloxybenzyl-1-[(1-hydroxy-3-amino-2-propoxy)methyl]barbiturate, 5-benzyloxybenzyl-1-[(2-(3-carboxypropionyloxy)ethoxy)methyl]-barbiturate, 5-benzyl-1-[(1-hydroxy-2-ethoxy)methyl]barbiturate, 5-methoxybenzylacetylbarbiturate, 5-benzyl-1-[(1,3-dihydroxy-2-propoxy)methyl]barbiturate, 5-benzyl-1-[(1-hydroxy-3-amino-2-propoxy)methyl]barbiturate, 5-benzyl-1-[(2-(3-carboxypropionyloxy)ethoxy)methyl]barbiturate, 5-methoxybenzylacetyl-acyclobarbiturate, 2,2'-anhydro-5-ethyluridine, and acyclouridine compounds like 5-benzyl-substituted acyclouridine derivates, for example, benzyla-cyclouridine, benzyloxy-benzyl-acyclo-uridine, aminomethyl-benzyl-acyclouridine, aminomethyl-benzyloxybenzyl-acyclouridine, hydroxymethyl-benzylacyclouridine or hydroxymethyl-benzyloxy-benzyl-acyclouridine.

Others are also known, e.g., in U.S. Pat. No. 5,567,689 and the references listed therein, particularly U.S. Pat. No. 4,613,604, U.S. Pat. No. 5,077,280 and/or U.S. Pat. No. 5,141,943.

Among inhibitors of uridine secretion are those compounds that inhibit the transport of uridine from the cells, particularly the renal clearance of uridine. This class particularly includes N,N'-bis[3-(3,4,5-trimethoxybenzoyloxy) propyl]-homopiperazine (Dilazep) or N,N'-dimethyl-N,N'-bis[3-(3',4',5'-trimethoxybenzoxy)propyl]-ethylendiamine (hexobendine), or other compounds listed in U.S. Pat. No. 5,567,689.

Compounds that compete with uridine in renal transport mechanisms are in particular L-uridine, L-2',3'-dideoxyuridine und D-2',3'-dideoxyuridine.

Especially preferred (possibly also over other mechanisms than those which work as those described) are pyrimidine nucleosides and/or prodrugs of them.

Pyrimidine nucleosides, are, in the first place, the ribonucleosides or the deoxyribonucleosides of uracil or cytosine, specifically uridine and/or cytidine, in addition of thymine, such as thymidine.

Prodrugs are, in the first place, the metabolic precursors of the named pyrimidine nucleosides from which the pyrimidine nucleosides are manufactured and/or released in the body. Those compounds that are preferred are those in which one or several of the hydroxy groups in the ribose radical are esterified, in each case with an acyl group, and/or amino groups (as in cytidine or deoxycitidine), when present, are acylated with acyl radicals, or intermediates of the pyrimidine nucleotide biosynthesis, which enter into the pyrimidine biosynthesis distal of the DHODH (such as orotic acid or its esters, for example, alkylester).

In addition, prodrugs can be selected from among triphenyl uridine, triphenyl cytidine, uridine- or cytidine-5'-monophosphate or prodrugs from them (e.g., mono- or dialkylesters, acyloxyalkylesters, alkoxycarbonylmethylesters, substituted ethyl- and propylesters, amidomethylesters, benzylesters, phenylesters, phosphonoamidates, cyclophosphatesters, such as cytidine diphosphocholine or uridine diphosphoglucose); and oligo- or polynucleotides are used with U and/or C as base building blocks, like homo- or heterodimeres (e.g., U-P-U, U-P-C, C-P-U or C-P-C, where P stands for the binding bivalent phosphoric acid radical).

Wherever the active agents are mentioned that increase the concentration of pyrimidine base building blocks for the synthesis of nucleic acids in the body, specifically pyrimidine nucleosides or their derivates, this refers, insofar as the named compounds contain saliferous groups, to the named compounds groups in free form and/or in the form of salts. Salts of pyrimidine nucleosides or their prodrugs are particularly pharmaceutically usable salts. If basic groups are present, like amino or imino, these can form acid addition salts, for example with inorganic acids like sulfuric acid or halogen hydrides or with organic acids, for example, carboxylic acids like acetic acid, or sulfonic acids like methane sulfonic acid. If acid groups are present, like carboxy or sulfo, these can form salts with cations, for example, of metals like alkaline or earth alkaline metals, e.g., potassium or sodium, or with amino- or ammonia compounds, ammonium ions or low-alkylamines. Inner salts, too, can be formed, if both acid and basic groups are present.

Halogen refers specifically to fluorine, chlorine, bromine, or iodine.

The prefix "low" means that the radical in question has preferably up to 7, specifically up to 4, carbon atoms.

"In addition" means "in a broader, specifically less preferred embodiment of the invention."

"To increase the concentration in the body" means specifically an increase of the concentration in the blood plasma, cells or their organelles, such as mitochondria, in the case of warm-blooded species, primarily humans.

Alkyl is in particular $C_1$–$C_{25}$-alkyl, preferably low-alkyl. The named radicals, such as alkanoyl, alkenoyl or alkinoyl, can be present in linear form, or in addition, in case the number of C-atoms allows it, in singly or multiply branched form.

Acyl is in particular the group of a carboxylic acid (especially preferred) that is bound by means of carbonyl to the binding oxygen (or, as in the case of cytidine, additionally to nitrogen) or of an unsubstituted or substituted amino acid (preferred); an acyl radical of a semi-ester of carbon dioxide linked by means of its carbonyl group to the binding oxygen or in addition nitrogen (preferred); or, in addition, an amino carbonyl group or an N-substituted amino carbonyl group. Acyl has preferably up to 25, primarily up to 20 carbon atoms, if not otherwise indicated.

The preferred acyl of a carboxylic acid is in particular unsubstituted or substituted $C_1$–$C_{25}$-alkanoyl, $C_3$–$C_{25}$-alkenoyl or $C_3$–$C_{25}$-alkinoyl, in particular low-alkanoyl, octanoyl, nonanoyl, decanoyl, undecanoyl, dodecanoyl or palmitoyl, or, in addition, substituted low-alkanoyloxy, in which situation the substitute components are, for example, selected from one or more radicals, preferably one to three radicals, in particular of one radical, in every case independently of one another, selected from among hydroxy, low-alkoxy, phenoxy, naphthoxy, low-alkanoyloxy, phenyl-low-alkanoyloxy, such as benzoyloxy or phenylacetyloxy, halogen, such as fluorine, chlorine, bromine or iodine, in particular fluorine or chlorine, carboxy, low-alkoxycarbonyl, phenyl-low-alkoxycarbonyl, such as benzyloxycarbonyl, carbamoyl, low-alkylcarbamoyl, hydroxy-low-alkylcarbamoyl, di-low-alkylcarbamoyl, bis(hydroxy-low-alkyl) carbamoyl, cyano, oxo, $C_3$–$C_8$-cycloalkyl, such as cyclopropyl, cyclobutyl, cyclopentyl or cyclohexyl, $C_6$–$C_{12}$-bicycloalkyl, such as decahydronaphth-2-yl, $C_9$–$C_{14}$-tricycloalkyl, such as 1- or 2-adamantyl, $C_4$–$C_8$-cycloalkenyl, such as 1-cyclohexenyl or 1,4-cyclohexadienyl; heterocyclyl, which preferably indicates a saturated, partially saturated, or unsaturated simple ring that contains 3 to 7, preferably 5 to 7, ring atoms, and that contains up to four heteroatoms, selected from among nitrogen, sulfur, and/or oxygen, preferably 1 or 2 of the named heteroatoms; in which case the ring is either present as such or can be as much as doubly, preferably singly, benz-anelated, cyclopenta-, cyclohexa- or cyclohepta-anelated; and which can be unsubstituted or substituted, in particular by low-alkyl, low-alkanoyl, hydroxy, low-alkoxy, phenyl-low-alkoxy, such as benzyloxy, hydroxy-low-alkyl, such as hydroxymethyl, halogen, cyano and/or trifluormethyl, e.g., pyrrolyl, 2,5-dihydropyrrolyl, furyl, thienyl, tetrahydrofuryl, cyclohepta[bipyrrolyl, pyrrolidinyl, imidazolyl, imidazolidinyl, pyrazolinyl, pyrazolidinyl, triazolyl, such as 1,2,3-, 1,2,4-or 1,3,4-triazolyl, tetrazolyl, such as 1- or 2-tetrazolyl, tetrahydro-oxazolyl, tetrahydro-isoxazolyl, tetrahydro-thiazolyl, tetrahydro-isothiazolyl, indolyl, isoindolyl, chinolyl, isochinolyl, benzimidazolyl, benzofuranyl, pyridyl, pyrimidinyl, piperidinyl, piperazine-1-yl, morpholino, thiomorpholino, S,S-dioxothiomorpholino, 1,2-dihydro- or 1,2,3,4-tetrahydrochinolyl, or 1,2-dihydro- or 1,2,3,4-tetrahydroisochinolyl, in which case the radicals mentioned are unsubstituted or are substituted as above, in particular by low-alkyl, e.g., in 4-low-alkyl-piperazine-1-yl, such as 4-methyl- or 4-ethyl-piperazine-1-yl, by low-alkanoyl, e.g., in 4-low-alkanoyl-piperazine-1-yl, such as 4-acetyl-piperazine-1-yl, or by hydroxy-low-alkyl, e.g., in 5-hydroxymethylfuran-2-ylcarbonyl, and aryl, preferably $C_6$–$C_{14}$-aryl, e.g., phenyl, naphthyl, such as 1- or 2-naphthyl, or fluorenyl, such as fluoren-9-yl, in which case aryl is unsubstituted or is substituted for example singly or multiply, preferably multiply, by low-alkanoyl, for example by low-alkyl, e.g., methyl, halogen-low-alkyl, such as trifluormethyl or chlorine or bromine methyl, halogen, e.g., fluorine or chlorine, hydroxy, low-alkoxy, such as methoxy, low-alkanoyloxy, carboxy, low-alkyloxycarbonyl, phenyl-low-alkoxycarbonyl, carbamoyl, mono- or di-low-alkylcarbamoyl, mono- or dihydroxy-low-alkylcarbamoyl, such as heterocyclyl-low-alkyl, in which case heterocyclyl is defined as above as a substituent of low-alkanoyl, in particular heterocyclylmethyl, in which heterocyclyl is bound by a ring nitrogen atom, e.g., piperidinomethyl, piperazine-1-ylmethyl, 4-low-alkyl-piperazine-1-ylmethyl, such as 4-methyl- or 4-ethyl-piperazine-1-ylmethyl; 4-low-alkanoyl-piperazine-1-ylmethyl; such as 4-acetyl-piperazine-1-ylmethyl, morpholinomethyl or -thiomorpholinomethyl, cyano and/or nitro, in particular phenyl, which is substituted by one of the radicals named in p-position, e.g., low-alkanoyl, such as formyl, acetyl, propionyl, pivaloyl or heptanoyl, such as n-heptanoyl, hydroxy-low-alkanoyl, e.g., beta-hydroxypropionyl, low-alkoxy-low-alkanoyl, e.g., low-alkoxyacetyl or low-alkoxypropionyl, such as methoxyacetyl or beta-methoxypropionyl, low-alkanoyloxy-low-alkanoyl, e.g., low-alkanoyloxyacetyl or low-alkanoyloxypropionyl, such as acetoxyacetyl or beta-acetoxypropionyl, halogen-low-alkanoyl, e.g., alpha-halogenacetyl, such as alpha-chlorine-, alpha-bromine-, alpha-iodine-, alpha,alpha,alpha-trifluar or alpha,alpha,alpha-trichloracetyl, or halogenpropionyl, such as beta-chlorine- or beta-bromine-propionyl, carboxy-low-alkanoyl, e.g., carboxyacetyl or 3-carboxypropionyl, low-alkoxycarbonyl-low-alkanoyl, e.g., low-alkoxycarbonylacetyl or low-alkoxycarbonylpropionyl, such as methoxycarbonylacetyl, beta-methoxycarbonylpropionyl, ethoxycarbonylacetyl, beta-ethoxycarbonylpropionyl, tert-butoxycarbonylacetyl or beta-tert-butoxycarbonylpropionyl, carbamoyl-low-alkanoyl, e.g., carbamoylacetyl or beta-carbamoylpropionyl, low-alkylcarbamoyl-low-alkanoyl, di-low-alkylcarbamoyl-low-alkanoyl, hydroxy-carboxy-low-alkanoyl, hydroxy-low-alkoxycarbonyl-low-alkanoyl, dihydroxy-carboxy-low-alkanoyl, dihydroxy-low-alkoxycarbonyl-low-alkenoyl, heterocyclyl-low-alkanoyl, for example pyrrolylcarbonyl, such as 2- or 3-pyrrolylcarbonyloxy, furyl-carbonyl, e.g., 2-furylcarbonyl, 5-hydroxymethyl-furan-2-ylcarbonyl, thienylcarbonyl, e.g., 2-thienylcarbonyl, imidazolocarbonyl, such as 4-imidazolylcarbonyl, imidazolylacetyl, such as 4-imidazolylacetyl, imidazolylpropionyl, such as 3-(4-imidazolylpropionyl, pyridylcarbonyl, e.g., 2-, 3- or 4-pyridyl-carbonyl, indolylcarbonyl, e.g., 2-, 3- or 5-indolylcarbonyl, 1-methyl-, 5-methyl-, 5-methoxy-, 5-benzyloxy-, 5-chlor- or 4,5-dimethylindolyl-2-carbonyl, chinolyl-carbonyl, such as chinoline-2-ylcarbonyl, pyrrolidinylcarbonyl, such as pyrrolidinyl-3-carbonyl, piperidinylcarbonyl, e.g., 2-, 3- or 4-piperidinylcarbonyl, morpholino-carbonyl, thiomorpholino-carbonyl, morpholinoacetyl, thiomorpholinoacetyl, or 4-low-alkyl-piperazinoacetyl, such as 4-methyl-piperazinoacetyl, low-alkenoyl, e.g., acryloyl, vinylacetyl, crotonoyl or 3- or 4-pentenoyl, low-alkinoyl, e.g., propinoyl or 2- or 3-butinoyl, $C_3$–$C_8$-cycloalkylcarbonyl or $C_3$–$C_8$-cycloalkylacetyl, e.g., cyclopropyl-, cyclobutyl-, cyclopentyl- or cyclohexyl-carbonyl, cyclopropylacetyl, cyclopentylacetyl or cyclohexylacetyl, phenyl-low-alkanoyl, e.g., benzoyl, phenylacetyl or 3-phenylpropionyl, in which case phenyl is unsubstituted or mono- or multiply substituted by low-alkyl, e.g., methyl, halo-low-alkyl, such as chlorine or bromine methyl, halogen, e.g., fluorine or chlorine, hydroxy, low-alkoxy, e.g., methoxy, piperidinomethyl, piperazln-1-ylmethyl, 4-low-alkyl-piperazine-1-ylmethyl, such as 4-methyl- or 4-ethyl-piperazine-1-ylmethyl, 4-low-alkanoyl-piperazine-1-ylmethyl, such as 4-acetyl-piperazine-1-ylmethyl, morpholino-low-alkyl, such as morpholinomethyl, thiomorpholino-low-alkyl, such as methyl, cyano and/or nitro, e.g., 4-chlormethyl-, 4-brom-methyl-, 4-fluor-, 4-chlor-, 4-methoxy-, 4-morpholinomethyl-, 4-thiomorpholinomethyl-, 4-cyano- or 4-nitrobenzoyl, or low-alkylphenylacetyl, such as 4-methyiphenylacetyl. Especially preferred are the acyl radicals of unsubstituted carboxylic acids, as defined above, or the acyl radicals of carboxylic acids physiologically present, such as glykoloyl, lactoyl, enolpyruvoyl, liponoyl, pantothenoyl, acetoacetoyl, p-aminobenzoyl, beta-hydroxybutyroyl, creatinoyl or orotoyl.

Preferred acyl of an acyl radical of a semi-ester of carbon dioxide connected to the binding oxygen by its carbonyl group is e.g., unsubstituted or substituted hydrocarbyloxycarbonyl, preferably with 2 bis 20 C-atoms, in particular unsubstituted or, in addition, substituted low-alkoxycarbonyl, e.g., methoxy-, ethoxy- or tert-low-alkoxycarbonyl, such as tert-butoxycarbonyl, 2-halogen-low-alkoxycarbonyl, e.g., 2-chlorine-, 2-bromine-, 2-iodine- or 2,2,2-trichlorethoxycarbonyl, aryl-low-alkoxycarbonyl, e.g., arylmethoxycarbonyl, in which case aryl preferably has 6 to 14 carbon atoms, is unsubstituted or is for example singly or multiply, preferably singly, substituted by low-alkyl, e.g.; methyl, halogen-low-alkyl, such as trifluormethyl or chlorine- or bromine-methyl, halogen, e.g., fluorine or chlorine, hydroxy, low-alkoxy, such as methoxy, low-alkanoyloxy, carboxy, low-alkyloxycarbonyl, phenyl-low-alkoxycarbonyl, carbamoyl, mono- or di-low-alkylcarbamoyl, mono- or di-hydroxy-low-alkylcarbamoyl, heterocyclyl-low-alkyl, in which case heterocyclyl is defined as above as a substituent for low-alkanoyl, in particular heterocyclylmethyl, in which case heterocyclyl is bound by a ring nitrogen atom, piperidinomethyl, piperazine-1-ylmethyl, 4-low-alkyl-piperazine-1-ylmethyl, such as 4-methyl- or 4-ethylpiperazine-1-ylmethyl, 4-low-alkanoyl-piperazine-1-ylmethyl, such as 4-acetyl-piperazine-1-ylmethyl, morpholinomethyl or thiomorpholinomethyl, cyano and/or nitro, and in particular phenyl, 1- or 2-naphthyl, fluorenyl or by low-alkyl, e.g., methyl or tert-butyl, low-alkoxy, e.g., methoxy, ethoxy or tert-butoxy, hydroxy, halogen, e.g., fluorine, chlorine or bromine, and/or nitro mono- or multiply-substituted phenylist, e.g., phenyl-low-alkoxycarbonyl, such as benzyloxycarbonyl, 4-methoxybenzyloxycarbonyl, 4-nitrobenzyloxycarbonyl, diphenyl-low-alkoxycarbonyl, such as diphenylmethoxycarbonyl, di-(4-methoxyphenyl)-methoxycarbonyl trityloxycarbonyl or fluorenyl-low-alkoxycarbonyl, such as 9-fluorenylmethoxycarbonyl or in addition heterocyclyl-low-alkoxycarbonyl, in which case heterocyclyl is defined as above as a substituent of low-alkanoyl, e.g., furan-2-ylmethoxycarbonyl or pyridine-2-, -3- or -4-ylmethoxycarbonyl.

A preferred N-substituted amino carbonyl group as acyl carries on its nitrogen 1 to 2 substituents, which are selected independently from one another from substituted or unsubstituted low-alkyl, in which case the substituents are selected from those named above for substituted low-alkanoyl and can be present in the number defined there, those substituents preferably being selected from among hydroxy, low-alkoxy, low-alkanoyloxy, phenyl-low-alkanoyloxy, such as benzoyloxy or phenylacetyloxy, halogen, such as fluorine, chlorine, bromine or iodine, in particular fluorine or chlorine, carboxy, low-alkoxycarbonyl, phenyl-low-alkoxycarbonyl, such as benzyloxycarbonyl, cyano, oxo and phenyl or naphthyl, which are unsubstituted or for example singly or multiply, preferably singly, substituted with low-alkyl, e.g., methyl, halogen-low-alkyl, such as trifluormethyl or chlorine- or bromine-methyl, halogen, e.g., fluorine or chlorine, hydroxy, low-alkoxy, such as methoxy, low-alkanoyloxy, carboxy, low-alkyloxycarbonyl, phenyl-low-alkoxycarbonyl, cyano and/or nitro, in particular phenyl, which is substituted with one of the named radicals in p-position; in particular from unsubstituted low-alkyl, such as methyl or ethyl; and aryl, which preferably has 6 to 14 carbon atoms, and is unsubstituted or for example singly or multiply, preferably singly, substituted by low-alkyl, e.g., methyl, halogen-low-alkyl, such as chlorine- or bromine-methyl, halogen, e.g., fluorine or chlorine, hydroxy, low-alkoxy, such as methoxy, low-alkanoyloxy, carboxy, low-alkyloxycarbonyl, phenyl-low-alkoxycarbonyl, halo-low-alkyl, such as trifluormethyl, cyano and/or nitro, in which case the nitrogen of the carbamoyl group no longer serves to bear an aryl radical. The definitions falling under the various definitions of acyl groups of an N-substituted carbamic acid and the aminocarbonyloxy radical can preferably be omitted.

A substituted or unsubstituted amino acid in acyl is formed, preferably by the amino acid groups (aminoacyl): of an alpha-, beta-, gamma- or delta-amino acid bound by the carbonyl of its carboxy group and an oxygen atom, in particular of a natural alpha-amino acid with the L-configuration, such as it normally occurs in proteins, or of an epimer of such an amino acid, i.e., with the unnatural D-configuration, or its D,L-isomer mixture; of a homologue of such an amino acid, e.g., in which case the amino acid side chain is lengthened or shortened by one or two methylene groups, in which case the amino group is present in beta-, gamma- or delta-position and/or in which case a methyl group is replaced by hydrogen; of a substituted aromatic amino acid, in which the aromatic radical has 6–14 carbon atoms, e.g., of a substituted phenylalanine or phenylglycine, in which case the phenyl-substituent can be low-alkyl, e.g., methyl, hydroxy, low-alkoxy, e.g., methoxy, low-alkanoyloxy, e.g., acetoxy, amino, low-alkylamino, e.g., methylamino, di-low-alkylamino, e.g., dimethylamino, low-alkanoylamino, e.g., acetylamino or pivaloylamino, low-alkoxycarbonylamino, e.g., carbon atoms, e.g., benzyloxycarbonylamino or 9-fluorenylmethoxycarbonylamino, halogen, e.g., fluorine, chlorine, bromine or iodine, carboxy and/or nitro, occurring singly or multiply; of a benz-anelated phenylalanine or phenylglycine, such as alpha-naphthylalanine, or of a hydrated phenylalanine or phenylglycine, such as cyclohexylalanine or cyclohexylglycine.

These amino acid groups can be substituted in free amino or hydroxy functions, as described above for amino acid groups R or Rg. Especially preferred is the radical of an amino acid bound by the carbonyl of its carboxy group and an oxygen atom, selected from among glycine, alanine, 2-amino butyric acid, 3-amino butyric acid, 4-amino butyric acid, 3-amino valeric acid, 4-amino valeric acid, 5-amino valeric acid, 3-amino caproic acid, 4-amino caproic acid or 5-amino caproic acid, valine, norvaline, leucine, isoleucine, norleucine (alpha-amino caproic-acid), serine, homoserine (alpha-amino-gamma-hydroxy butyric acid), threonine, methionine, cysteine, proline, trans-3- and trans-4-hydroxyproline, phenylalanine, tyrosine, 4-amino phenylalanine, 4-chlorphenylalanine, 4 carboxyphenylalanine, beta-phenylserine, phenylglycine, alpha-naphthylalanine, cyclohexylalanine, cyclohexylglycine, tryptophan, indolin-2-carboxylic acid, 1,2,3,4-tetrahydroisochinolin-3-carbon acid, asparagine acid, asparagine, amino malon acid, amino malon acid-monoamid, glutamine acid, glutamine, histidine, arginine, lysine, 8-hydroxylysine, ornithine, 3-aminopropan acid, alpha,gamma-diamino butyric acid and alpha,beta-diaminopropionic acid; especially preferred is the radical of an aliphatic amino acid, selected from among alanine, valine, norvaline, leucine, 3-aminopropion acid, 2-amino butyric acid, 3-amino butyric acid, 4-amino butyric acid, 3-amino valeric acid, 4-amino valeric acid, 5-amino valeric acid, 3-amino caproic acid, 4-amino caproic acid or 5-amino caproic acid and isoleucine or of an amino acid selected from among glycine, asparagine, glutamine, methionine, lysine, histidine, proline, carnitine and phenylalanine, in which case (except in instances in which there is no asymmetric carbon atom present, e.g., as with glycine) each of the named amino acids in the D-, L- or (D,L)-, preferably in the L-Form can be present, and an amino group is present, unsubstituted or singly or doubly, or triply, N-alkyliert, e.g., by low-alkyl, such as methyl, n-propyl or n-butyl, by pyridyl-low-alkyl, such as 2-, 3- or 4-pyridylmethyl, and/or by phenyl-low-alkyl, such as benzyl, in which case the carnitine radical is preferred and/or N-acylated, e.g., by unsubstituted or substituted low-alkanoyl, as defined for low-alkanoyl, primarily by acetyl, propionyl or pivaloyl, aryl-low-alkanoyl, e.g., phenyl-low-alkanoyl, such as benzoyl or phenylacetyl, by low-alkoxycarbonyl, such as tert-butoxycarbonyl, or by aryl-low-alkoxycarbonyl, e.g., phenylnlederalkoxycarbonyl, such as benzyloxycarbonyl. Of the latter radicals, the preferred ones are acyl groups of an unsubstituted or substituted amino acid selected from among aminoacetyl (glycyl), N-low-alkylaminoacetyl, N,N-di-low-alkylaminoacetyl, N-low-alkyl-N-phenyl-low-alkylaminoacetyl, N-low-alkyl-N-low-alkoxycarbonylaminoacetyl and N-phenyl-low-alkoxycarbonyl-N-low-alkylaminoacetyl, e.g., N-methylaminoacetyl, N,N-dimethylaminoacetyl, N-methyl-N-(n-butyl)aminoacetyl, N-methyl-N-benzylaminoacetyl, N-methyl-N-[(2-, 3- or 4-)pyridylmethyl-aminoacetyl, such as N-methyl-N-3-pyridylmethylaminoacetyl, N-methyl-N-tert-butoxycarbonylaminoacetyl, N-benzyloxycarbonyl-N-low-alkylaminoacetyl, prolyl, histidyl, glutamyl, asparagyl and carnitinoyl, in which case the amino acid radicals (except in cases in which there is no asymmetric carbon atom present, e.g., as in the case of gly) are present, preferably in the (L)-, in addition, in the (D)- or (D,L)-form.

The usable prodrugs or pyrimidine nucleosides according to the present invention are specifically those of the formulas I (uridine or the prodrugs of it) or II (cytidine or the prodrugs of it),

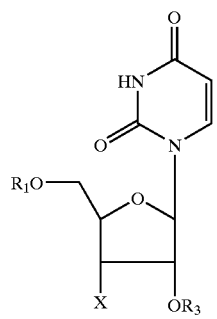

(I)

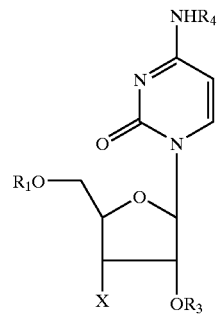

(II)

in which X stands for hydrogen or —$OR_2$, and $R_1$, $R_2$, $R_3$ and, when present, $R_4$, are selected independently of one another, from hydrogen and acyl (preferably the acyl radicals described as preferred).

The usable pyrimidine nucleosides or prodrugs according to the present invention are known in the art, commercially available or can be manufactured in accordance with known methods, e.g. according to or analogous to those in U.S. Pat. No. 5,968,914, U.S. Pat. No. 5,583,117, U.S. Pat. No. 5,567,689, WO 00/11952, or EP 0 604 368. The cited references are herewith incorporated by reference, specifically regarding the acyl groups and their introduction, and, insofar as described, the prodrugs for pyrimidine nucleosides and their administration and formulation.

Inhibitors of the biosynthesis of nucleic acids (like DNA or RNA) or their precursors (for example, nucleotides, deoxynucleotides, or in a given case the mono-, di- or tri-phosphates from them) specifically include:

inhibiting substances of ribonucleoside-diphosphate-reductase, primarily hydroxy urea (hydroxycarbamide; e.g., Litalirg, Bristol-Myers Squibb), Didox or Trimidox;

inhibitors of purine biosynthesis, such as 2-morpholinoethyl-(E)-6-(1,3-dihydro-4-hydroxy-6-methoxy-7-methyl-3-oxoisobenzofuran-5-yl)-4-methyl-4-hexenoate (Mycophenolat.Mofetil; e.g.,CellCept®, Hoffmann-LaRoche);

inhibitors of dihydrofolate-reductase, e.g., methotrexate, pyrimethamine, proguanil, cycloguanil or trimethoprim; or preferably, inhibiting substances of mitochondrial gamma-polymerase, specifically inhibiting substances of reverse transcriptase (RT), for example of HIV, specifically nucleoside analogue RT inhibitors (NRTI's), first and foremost AZT* (zidovudine=3'-azido-3'-deoxythymidin; e.g., Retrovir®; Glaxo-SmithKline), didanosine* (ddI, 2',3'-dideoxyinosine; e.g., Videx®; BMS), zalzitabine* (ddC, dideoxycytidine; e.g., HIVID Roche®), lamivudine* (2'-Deoxy-3'-thiacytidine, 3TC; e.g., Epivir®; Glaxo-SmithKline), Stavudin* (d4T=2',3'-didehydro-2', 3'-dideoxythymidine, e.g., Zerit®; BMS), Abacavir (e.g., Ziagen®; Glaxo-SmithKline); or d4C (2',3'-didehydro-2', 3'-dideoxycytidin), or in addition FTC (emtricitabine, Covirazil=fluoridated 3TC; Triangle/Abbott); DAPD (guanosine analogues; Triangle/Abbott) as well as its de-aminated metabolite DXG; fozivudine tidoxil (thioether-lipid-Zidovudin conjugate); ACH-126,443 (b-L-Fd4C, Achillion); Fosphazid (Phosphonavir, PZT); tenofovir* (PMPA), lodenosine (FddA, ddA), BCH-10618 (BioChemPharm), BCH-20652/dOTC (3TC-relative, BioChemPharm), BCH-13520, in which case all those compounds marked-with asterisks ("*") are preferred in the respective case;

or, in addition, other anti-viral nucleoside analogues (inhibitors of further viruses), e.g., nucleoside-analogous inhibiting substances of the hepatitis B virus, of the hepatitis C virus, of the CMV virus, of other herpes viruses, e.g., varizella-zoster virus, of the herpes simplex viruses, of the Epstein-Barr virus, of the HHV type 6, and the HHV type 8) as well as of the JC virus (e.g., acyclovir, penciclovir, sorivudine, valacyclovir, famciclovir) (e.g., Famvir; Glaxo-SmithKline), brivudine (e.g., Helpin®, Berlin-Chemie), entecavir (BMS-200475), trifluridine (TFT; e.g., Thilo®), idoxuridine (IDU; e.g., Synmiol®), but first and foremost fieluridine, ribavirin (e.g., Rebetol®; Essex), ganciclovir (e.g., Cymeven®), cidofovir (e.g., Vistide®) and adefovir dipivoxil (e.g., Adefovir®; Gilead);

or combinations of two or more of these inhibiting substances, and/or in addition, combinations of one of the above-named inhibiting substances with inhibitors of dihydro-orotic acid-dehydrogenase, e.g., with Leflunomid (e.g., Arava®; Aventis; on the basis of the long half-life period, it is specifically possible to reactivate cells of the immune system several days after the administration of leflunomide through an administration according to the present invention) or brequinar.

The medications (=pharmaceutical preparations) according to the invention can be administered to warm-blooded species (humans and animals) nasally, rectally, orally, parenterally, intramuscularly, or intravenously, and contain a dosage of the pharmacological active agent alone, or together with a significant quantity of a pharmaceutically applicable vehicle. The dosage of the active agent depends on the warm-blooded species, body weight, age and the individual's condition, the individual pharmokinetic facts, the disease to be treated, as well as the mode of application.

The dosage of the active agents that increase the concentration of pyrimidine base building blocks for the biosynthesis of nucleic acids in the body in warm-blooded species, specifically in humans, is particularly in the range between 1 mg and 15 g per m\2 of body surface per day; for uridine phosphorylase inhibitors, the concentration is preferably in the range of 10 mg to 1 g per day, divided into one to three doses; for inhibiting substances of the uridine secretion, the dosage is preferably in the range between 1 to 5 mg/kg of body weight one to three times a day; for compounds that compete with uridine in renal transport mechanisms, the doses administered are preferably in the range of 5 to 50 mg/kg of body weight; administered one to three times daily.

The pyrimidine nucleosides and/or prodrugs of them are administered in such doses that the blood plasma concentrations can be adjusted to lie between 10 and 500 $\mu$M, specifically between 20 and 300 $\mu$M, primarily between 25 and 250 $\mu$M, e.g., 50–200 $\mu$M. The determination of the blood plasma concentration takes place according to methods which are known in the art, preferably through use of HPLC at specific points in time after the administration of the pyrimidine nucleosides or the prodrugs from them, e.g., 1, 2, 3, 4 and 5 hours after administration, for example as described in U.S. Pat. No. 5,583,117.

Pyrimidine nucleo sides and/or prodrugs of them, specifically uridine, cytidine, primarily mono-, di- or tri-acyluridine or mono-, di-, tri- or tetra-acyluridine, are preferably administered daily in quantities from 10 to 500 mg/kg of body weight, specifically between 50 and 300 mg/kg daily, for example, divided into two or three separate doses, which are ingested in intervals of between 6 and 12 hours. The acyl derivates are more easily absorbed when taken orally, and are therefore preferred for oral administration.

The medications for use in accordance with the invention encompass specifically one or several of the mitochondrial reactivators, specifically those named as preferred, together with standard pharmaceutical vehicles.

The active agents can be used, e.g., for the manufacture of pharmaceutical preparations that contain an effective quantity of the active agent, together or in a mixture with a significant quantity of inorganic or organic, solid or liquid pharmaceutically usable vehicles.

The invention also relates to a pharmaceutical compound (preparation) that is suitable for administration to warm-blooded species, specifically humans, for the treatment or prevention of the side effects named above and below, specifically as regards HAART, primarily in connection with the administration of NRTI's, or in connection with the treatment with other anti-viral nucleoside analogues, including a quantity of a mitochondrial reactivator sufficient to effect a reduction or elimination of the side effects, together with at least one pharmaceutically acceptable vehicle.

The invention further relates to a method for the therapeutic or prophylactic activation of the biosynthesis of mitochondrial DNA (mtDNA) before, during, or after the administration of inhibitors of the biosynthesis of nucleic acids or their precursors, specifically those named as preferred, specifically also for the prevention of and therapy for primarily the side effects named below, in the first place those mitochondriopathies caused by the depletion of mtDNA in the context of perinatal transmission prophylaxis with inhibitors of the biosynthesis of nucleic acids or derivates of them; and/or a method for the therapeutic or prophylactic treatment of the side effects of inhibitors of the biosynthesis of nucleic acids or their precursors, specifically those named as preferred, which result from an inhibition of the orotate dehydrogenase and/or the biosynthesis of mtDNA, in connection with which the side effects are manifest, specifically those of lipodystrophy, changes in the sperm and/or osteopenia, in addition, liver damage (primarily micro- or macro vesicular steatosis, steato-hepatitis up to and including liver failure), hyperlacticemia/lactic acidosis, pancreatitis, disorder of the kidney function (including Fanconi syndrome) and/or diminished aerobic endurance, which arise in connection with the use of inhibitors of the biosynthesis of nucleic acids or their precursors, primarily in connection with HAART, particularly by the administration of NRTI's, or in connection with therapy with other anti-viral nucleoside analogues, in connection with which a therapeutically or prophylactically effective quantity of an active agent that increases the concentration of pyrimidine building blocks for the synthesis of nucleic acids in the body, specifically one described as preferred, or a pharmaceutically usable salt of it, in a dosage effective for the treatment of the named side effect, specifically to a warm-blooded species, e.g., a human, who requires the treatment because of one of the named side effects.

The pharmaceutical preparations contain from approximately 1% to approximately about 96%, preferably from approximately 20% to approximately 90%, of one or several active agents that increase the concentration of pyrimidine base building blocks for the biosynthesis of nucleic acids in the body (referred to below as an "active agent"). According to the present invention, pharmaceutical preparations can be, e.g., in single dose form, solutions of infusions ready for use, ampoules, vials, suppositories, dragées, tablets, or capsules.

The pharmaceutical preparations in the present invention are prepared in known ways, e.g., by conventional processes for solutions, freeze-drying, mixing, granulating, or the preparation of dragées.

For parenteral use, it is preferable to use capsules or solutions of the active agent, also suspensions, particularly isotonic aqueous solutions or suspensions, which can be prepared before use, e.g., in the case of lyophilized preparations, which contain the active agent alone or together with a vehicle, e.g., manna sugar. The pharmaceutical preparations can be sterilized and/or contain processing materials, e.g., preservatives, stabilizers, moisturizers and/or emulsifiers, solvents, salts for the regulation of osmotic pressure and/or buffers or acids, e.g., citric acid, and are manufactured in a well-known manner, e.g. by means of conventional solution or freezing processes. The named solutions or suspensions can contain substances that increase viscosity, such as sodium carboxymethyl cellulose, carboxymethyl cellulose, hydroxypropylmethyl cellulose, silica gel, dextran or polyvinylpyrrolidon.

Suspensions in oil contain as oleagenous components the vegetable, synthetic, or semi-synthetic oils that are customary for injection purposes, particularly fatty acid esters, which, as acid components, contain a long-chain fatty acid with 8–22, specifically 12–22 carbon atoms, e.g., lauric acid, palmitic acid, stearic acid or arachidonic acid, or corresponding unsaturated acids, e.g., oleic acid or linoleic acid, in a given case with the addition of antioxidants such as vitamin E, beta-carotene, or 3,5-di-tert-butyl-4-hydroxy-toluol. The alcohol component of these fatty acid esters has a maximum of 6 carbon atoms and is a mono-or multihydric, e.g., mono-, di- or tri-hydric, alcohol, e.g., ethanol, isopropyl alcohol, but primarily glycol and glycerine. As fatty acid esters, therefore, the following examples can be named: ethyl oleate, isopropyl myristate, isopropyl palmitate, polyoxyethylene glycerintrioleate, triglycerides of saturated fatty acids of a chain length $C_8$ to $C_{12}$, but especially vegetable oils like sesame seed oil.

The manufacture of preparations for injection takes place in the customary manner under sterile conditions, as does the filling into ampoules or vials and the sealing of the containers.

Pharmaceutical preparations for oral use can be obtained by combining the active agent with stable vehicles, if desired, granulating a prepared mixture and, if desired, processing the mixture into tablets, dragée kernels, or capsules after the addition of suitable processing materials. In this connection, synthetic vehicles can be included in them, which release the active agents in regular doses or cause them to be diffused.

Suitable vehicles include specifically fillers like sugar, e.g., lactose, saccharose, manna sugar, or sorbitol, cellulose preparations, or calcium phosphate, in addition, binders like starch paste, using corn or potato starch, gelatins, tragacanth, methyl cellulose, hydroxypropylmethylcellulose, sodium carboxymethyl cellulose and/or polyvinylpyrrolidon, and/or, if desired, dispersion agents like the above-named starches, in addition, carboxyl methyl starch, cross-linked polyvinyl pyrrolidon, agar, agaric acid or its salt, such as sodium alginate. Additives are first and foremost viscosity regulators and lubricants, e.g., silica gel, talcum, stearic acid or its salts, as magnesium or calcium stearate, and/or polyethylene glycol. Dragée kernels are provided with suitable coatings, if necessary, which resist the stomach acids.

Capsules are two-part capsules of gelatin, as well as soft, closed capsules of gelatin and a softener, such as glycerine or sorbitol. The two-part capsules can contain the active agent in the form of a granulate, e.g., with fillers like lactose, binders like starches, and/or lubricants like talcum or magnesium stearate, and possibly with stabilizers. In capsules, the active agent is preferably dissolved or suspended in suitable oleaginous processing materials like fatty oils, paraffin oil or liquid polyethylene glycols, in which case stabilizers and/or antibacterial agents can likewise be added. Stabilizers, like emulsifiers, surfactants, or tensides, binders like starch paste, tragacanth, or methylcellulose, hydroxypropylmethyl cellulose, sodium carboxymethyl cellulose, cyclodextrin and/or polyvinylpyrrolidon, and/or antibacterial agents can be added. Possible emulsifiers include oleic acid, non-ionic tensides of the fatty acid type-polyhydroxy alcohol ester like sorbitol monolaurate, -oleate, -stearate or -palmitate, sorbitan tristearate or -trioleate, polyoxyethylene addition compounds of fatty acid-polyhydroxy alcohol esters, like polyoxyethylene sorbitan monolaurate, -oleate, -stearate, -palmitate, -tristearate or -trioleate, polyethylene glycol fatty acid esters like polyoxyethyl stearate, polyoxyethylene glycol-(300 or 400)-stearate, polyethylene glycol-2000-stearate, or ethylene oxide-propylene oxide-block polymers.

Coloring or pigments can be added to the capsule or dragée coatings, e.g., for the purposes of identification or indication of different active-agent doses.

The administration can be parenteral as well as intravenous (for example, by intramuscular, subcutaneous, or specifically intravenous injection, by infusion or, specifically if toxic symptoms appear, like phlebitis of a peripheral vein, by central vein catheter), specifically in the case of acute lactic acidosis or liver failure, otherwise enteral, specifically oral.

The invention also relates to combinations of (A) active agents that increase the concentration of pyrimidine base building blocks for the biosynthesis of nucleic acids in the body, with (B) one or several other active agents, specifically with anti-viral active agents as those in HAART, preferably NRTI's, or with other anti-viral nucleoside analogues used for the treatment of infections with other viruses, in particular the above-named. In particular, the invention includes combinations or products that contain the active agents named under (A) and one or several of the active agents named under (B), either in a fixed combination or staggered over a period of time, or for simultaneous use in a joint kit.

Products in which the therapeutica are available in a joint kit with the preparations that contain the mitochondrial reactivator are also suitable for the treatment of side effects at intervals in treatment using the anti-viral therapy (interruption of HAART, specifically interruption of the therapy with NRTI's or with other nucleoside analogues).

In addition to the named inhibitors of the biosynthesis of nucleic acids or their precursors, further therapeutic agents, specifically for the treatment of AIDS, can be used simultaneously or in a staggered manner over time, such as entry inhibitors, CD4-binding inhibitors, chemokine receptor antagonists, HIV-protease inhibitors, CXCR-4 antagonists, fusion inhibitors, non-nucleoside-analogous RT inhibitors (e.g., MKC-442 (Emivirin), SJ-3366 (Samjin Pharmaceuticals), TMC120 (Tibotec), UC-781 (Uniroyal), PNU-242721 (Pharmacia & Upjohn, Calanolide-A (SarawakMed), DPC-963,083 (DuPont), UIC-94-003, AG-1549 (Capravirin; Agouron), GW420867X (Glaxo-Wellcome), DPC-961 (DuPont)), pyrophosphate analogues, integrase inhibitors, zinc finger inhibitors, interferons and tat/Rev inhibitors; as well as further therapeutic agents such as antibiotics (for example for therapy for secondary infections in the case of AIDS) or other chemotherapeutic agents. Corresponding pharmaceutical preparations can likewise be kits, in Which several active agents for simultaneous or staggered administration are jointly present as pharmaceutical formulations or as fixed combinations.

PREFERRED EMBODIMENTS OF THE INVENTION

Preferred embodiments of the invention can be found in the use of more specific definitions for general expressions and symbols in the above embodiments. Further preferred embodiments are found in the dependent claims.

Where the claims discuss uses, it is also possible, instead, to use the corresponding combinations or products for the administration of active agents which increase the concentration of pyrimidine base building blocks for the biosynthesis of nucleic acids in the body, specifically pyrimidine nucleosides and/or prodrugs of them, with inhibitors of the biosynthesis of nucleic acids or their precursors, the methods for the treatment of side effects of inhibitors of the biosynthesis of nucleic acids or their precursors using the named active agents, specifically pyrimidine nucleosides and/or prodrugs or named combinations or products, or corresponding pharmaceutical preparations, which defines the preferred embodiments of the invention in each case.

EXAMPLES

The following examples serve the purpose of explaining the invention, without limiting its scope.

Example 1

Compensation of the ddC-caused Depletion of mtDNA in Liver Cell Lines Through Uridine Cell culture. The HepG2 cell line, a human hepatoma cell line, is taken from the American Type Culture Collection (ATCC No. HB-8065). It is cultured at 37° C. in a 5% $CO_2$ atmosphere. The culture medium is Dulbecco's Modified Eagle Medium (DMEM-containing 4.5 g/l glucose, 110 mg/l pyruvate, 4 mg/l nicotinamide, 4 mg/l pyridoxal hydrochloride, 4 mg/l thiamine and 0.4 riboflavin), supplemented with 10% fetal bovine serum (50 ml FCS, Mycoplex PAA Laboratories, Linz). On day 1, $2.7 \times 10^6$ cells are placed in 75 ml culture flasks (Falcon, Becton Dickinson, USA). On days 5, 10, 15, 20 and 25, the cells are trypsinized and counted; $2.7 \times 10^6$ cells are again spread out. The medium is changed on each day of trypsinization and on the third day after replating.

Materials: Riboflavin (vitamin $B_2$), thiamine (vitamin $B_1$), ascorbic acid (vitamin C), uridine and ddC are purchased from Sigma (USA). The concentrations of uridine are given in the following tables; ddC is used in a concentration of 177 nM, which corresponds to the steady-state plasma levels of patients under HAART. A vitamin cocktail consisting of 7.125 mg/l riboflavin, 7.125 mg/l thiamine and 142.5 mg/l vitamin C is used. These pharmacological concentrations exceed the daily requirement by a factor of about one hundred, and meet the safe upper limits according to the recommendations of the European Union for these micronutrients.

Determining the intracellular lipids: Intracellular lipid droplets' are stained by means of Oil-Red-O (Sigma, USA). The cells are laid out on cover glasses, incubated with Oil-Red-O (Sigma, USA) for 30 minutes and counterstained with Meyer's hematoxylin (8 min.), then washed with water and embedded in glycerin gelatin.

Lactic acid: 1.5 ml of the remainder of the culture is removed in each case immediately before the trypsinization and the L-lactate in it is determined enzymatically with the lactate test-kit from Roche Diagnostics (order No.1822837) in an automatic analysis device (Roche/Hitachi 917) according to the recommendations of the manufacturer.

Quantification of mitochondrial DNA (mtDNA) by means of Southern Blot: The content of mtDNA is determined by a well-known Southern-Blot technique (C. T. Moraes et al., "Quantitative Defects of Mitochondrial DNA", in: S. DiMauro and D. C. Wallace, "Mitochondrial DNA in Human Pathology", Raven Press, New York 1993, Chapter 8, pages 97–108). Genomic DNA is extracted from the fatty tissue and cut with the restriction endonuclease PvuII. Five $\mu$g of the cut material are separated electrophoretically on a 0.8% agarose gel and transferred to a nylon membrane. The mtDNA is tested with a 12.9 kBp mtDNA fragment (which comprises the nucleotide positions 3470 and 16379 of human mtDNA (S. Anderson et al., Nature 9, 457–65 (1981), and which is marked by means stochastically binding primers with digoxigenin). In order to have an internal standard, digoxigen labeled nuclear DNA (nDNA), which hybridizes to the copy-number 18S-ribosomal DNA gene, serves as a second probe. The signals for mtDNA and nDNA are visualized, according to the recommendations of the manufacturer (Boehringer Mannheim, Germany), with a monoclonal antibody against digoxigenin, which is conjugated with alkaline phosphatase. The signal intensities are quantified by computer by means of standard software. The mtDNA content is expressed as the mtDNA/nDNA (M/N) ratio.

Results: Apart from a short lag-phase after trypsinization, the HepG2-cells show logarithmic growth during the entire 25-day incubation period.

Uridine in a concentration of 200 $\mu$M normalizes the survival of the HepG2-cells in the presence of ddC, as can be seen from Table 1:

TABLE 1

Number of cells (in 100,000s) on the day of the trypsinization (day 0 = 100%)

| | Day 0 | Day 5 | Day 10 | Day 15 | Day 20 | Day 25 |
|---|---|---|---|---|---|---|
| HepG2-cells without NRTI, without uridine | — | 129.2 (SD = 15.8) | 121.5 (SD = 12.3) | 118.5 (SD = 13.7) | 121.5 (SD = 7.9) | 127.4 (SD = 13.8) |
| ddC 177 nM | — | 110.0 | 98.5 | 92.1103.0 | 66.2 | 38.4 |
| ddC 177 nM + uridine 200 $\mu$M | — | 122.4 | 132.0 | 114.4 | 120.2 | 130.6 |
| ddC 177 nM + vitamins | — | 124.0 | 106.4 | 58.8 | 43.4 | — |

SD = standard deviation (n = 7)

Uridine diminishes the reduction of the mtDNA; see Table 2.

TABLE 2

Content of mitochondrial DNA, expressed as an M/N-ratio in % of the control (HepG2-cells without ddC and without uridine)

| | Day 0 | Day 5 | Day 10 | Day 15 | Day 20 | Day 25 |
|---|---|---|---|---|---|---|
| ddC 177 nM | 100.0 | 25.6 | 25.1 | 11.5 | 8.3 | 8.4 |
| ddC 177 nM + uridine 200 M | 100.0 | 74.7 | 60.4 | 64.2 | 53.1 | 67 |
| ddC 177 nM + vitamins | 100.0 | 16.0 | 8.9 | 9.7 | 9.3 | — | n.d. = not measured.

The production of lactic acid, which appears as the result of increased compensatory glycolysis and an NADH/NAD equilibrium shift in favor of NADH because of the inhibition of the mitochondria) oxidative phosphorylation by the inhibitors of the gamma-polymerase, is diminished by the uridine; see Table 3.

TABLE 3

Lactate values in the medium in percent of the control (without ddC and without uridine) - Day 0 = 100%

| | Day 0 | Day 6 | Day 10 | Day 15 | Day 20 | Day 25 |
|---|---|---|---|---|---|---|
| ddC 177 nM | — | 109.2 | 129.5 | 220.1 | 374.9 | 392.5 |
| ddC 177 nM + uridine 200 μM | — | 101.5 | 99.1 | 100.7 | 106.6 | — |
| ddC 177 nM + vitamins | — | 196.1 | 143.0 | 249.0 | 302.1 | — |

In measuring the intracellular lipids, on Day 20 there is a clear diminution of steatotic changes in the presence of uridine. While in the presence of 177 μM of ddC and 200 μM of uridine, the microscopic image resembles that of the control without ddC and without uridine (many cells, little red color from Oil-Red-O), in the presence of 177 μM ddC (without uridine) clearly fewer cells are found, which however, are relatively large and red-colored (=containing fat). In the presence of 177 μM ddC and the vitamin cocktail, the image attained resembles that in the presence of 177 μM ddC without uridine. Thus it is solely the presence of the uridine which can compensate for the side effects of ddC. Supplementing with vitamins, on the other hand, produces no recognizable favorable effect (see also Tables 1 to 3).

Example 2

Compensation for the NRTI-Stipulated Depletion in mtDNA in Liver Cell Lines through Uridine Analogously to Example 1, experiments were carried out with ddI and with d4T instead of ddC.

Example 3

Example of Formulation for an Infusion Solution with Uridine

In a concentration of 10 mg/ml, uridine is diluted in 100 ml of a 0.9% salt solution according to the US Pharmacopoeia under sterile conditions, and the resulting infusion solution is used for infusion.

Example 4

Tablets with Triacetyluridine

The following ingredients are used for the manufacture of 5000 tablets, each of which contains 200 mg of triacetyluridine (for the manufacturing process, see U.S. Pat. No. 5,538,117):

| | |
|---|---|
| Triacetyluridine | 1000 g |
| Corn starch | 680 g |
| Colloidal silica gel | 200 g |
| Magnesium stearate | 20 g |
| Stearic acid | 50 g |
| Sodium carboxymethyl starch | 250 g |
| Water | as much as is necessary |

A mixture of triacetyluridine, 50 g of cornstarch, and the silica gel is processed together with the starch paste, which consists of 250 g of cornstarch and 2.2 kg of demineralized water, thereby producing a moist mass. This is pressed through a sieve with a mesh size of 3 mm and dried for 30 min. in a fluidized bed dryer at 45° C. The dried granulate is pressed through a sieve with a mesh size of 1 mm, mixed with a mixture of 300 g corn starch, the magnesium stearate, the stearic acid, and the sodium carboxymethyl cellulose that was previously passed through a 2 mm sieve, and compressed into slightly rounded tablets.

What is claimed is:

1. A method of treating or preventing lipodystrophy resulting from administering NRTI's to a subject, said method comprising administering to a subject in need thereof an effective amount of one or more active agents selected from the group consisting of pyrimidine nucleosides or their prodrugs, and salts thereof.

2. The method according to claim 1, wherein said subject in need there of is a warm-blooded species.

3. The method according to claim 1, wherein said one or more active agents are selected from the group consisting of orotic acid, uracil, cytosine, and thymine.

4. The method according to claim 1, wherein the prodrugs are those of the following formulas I or II, in which X is hydrogen or —OR$_2$, and R$_1$, R$_2$, R$_3$ and, if present, R$_4$ is independently hydrogen or acyl, with at least one of the radicals R$_1$, R$_2$, R$_3$ and R being an acyl:

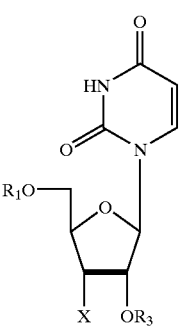

(I)

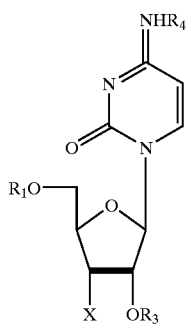
(II)
5. The method according to claim 1, wherein said lipodystrophy comprises lipoatrophy, dyslipidemia, and insulin resistance.
6. The method according to claim 1, wherein said subject in need thereof is a fetus or a child after birth in the first year of life.
7. The method according to claim 1, wherein said subject in need thereof is a human.
* * * * *

(12) EX PARTE REEXAMINATION CERTIFICATE (7244th)
United States Patent
Walker

(10) Number: US 6,992,072 C1
(45) Certificate Issued: Dec. 15, 2009

(54) COMBATING SIDE-EFFECTS

(75) Inventor: Ulrich Walker, Freiburg (DE)

(73) Assignee: Pharma Nord APS, Vojens (DK)

Reexamination Request:
No. 90/008,908, Oct. 30, 2007

Reexamination Certificate for:
| | |
|---|---|
| Patent No.: | 6,992,072 |
| Issued: | Jan. 31, 2006 |
| Appl. No.: | 10/468,846 |
| Filed: | Feb. 11, 2004 |

(22) PCT Filed: Feb. 27, 2002

(86) PCT No.: PCT/DE02/00721

§ 371 (c)(1),
(2), (4) Date: Feb. 11, 2004

(87) PCT Pub. No.: WO02/069943

PCT Pub. Date: Sep. 12, 2002

(30) Foreign Application Priority Data

Mar. 3, 2001 (DE) ............................................ 10110355

(51) Int. Cl.
| | |
|---|---|
| *A61K 31/7068* | (2006.01) |
| *A61K 31/7072* | (2006.01) |
| *A61K 31/70* | (2006.01) |
| *A61K 31/7052* | (2006.01) |

(52) U.S. Cl. ........................... 514/49; 536/28.5; 514/42; 514/43; 514/50

(58) Field of Classification Search ........................ None
See application file for complete search history.

(56) References Cited

FOREIGN PATENT DOCUMENTS

| WO | WO 93/01202 A1 | 1/1993 |
| WO | WO 00/50043 A1 | 8/2000 |

OTHER PUBLICATIONS

Stryer, Biochemistry, 2nd edition (W.H. Freeman and Co. 1981) pp. 512–513.*

Blanche et al., "Persistent mitochondrial dysfunction and perinatal exposure to antiretroviral nucleoside analogues," *Lancet,* 354: 1084–1089 (1999).

Brinkman et al., "Mitochondria toxicity induced by nucleoside–analogue reverse–transcriptase inhibitors is a key factor in the pathogenesis of antiretroviral–therapy–related lipodystrophy," *Lancet,* 354: 1112–1115 (1999).

Carr et al., "A syndrome of lipodystrophy (LD), lactic acidaemia and liver dysfunction associated with HIV nucleoside analogue reverse transcriptase inhibitor therapy: contribution to PI–related LD syndrome," *Antiviral Therapy,* 4(Suppl. 2):33 (abstract No. 11) (1999).

Kakuda et al., "Nucleoside reverse transcriptase inhibitor–induced mitochondrial toxicity as an etiology for lipodystrophy," *AIDS,* 13(16): 2311–2312 (1999).

Mallal et al., "Contribution of nucleoside analogue reverse transcriptase inhibitors to subcutaneous fat wasting in patients with HIV infection," *AIDS,* 14(10): 1309–1316 (2000).

Miro et al., "Respiratory chain dysfunction associated with multiple mitochondrial DNA deletions in antiretroviral therapy–related lipodystrophy [Research Letters]," *AIDS,* 14(12): 1855–1857 (2000).

Van Der Valk et al., "Increased risk of lipodystrophy when including NRTIs in the treatment of HIV–1 infection with protease inhibitors: results from a randomized controlled trial," *Antiviral Therapy,* 5(Suppl. 5):70 (abstract No. P78) (2000).

Walker et al., "Decrease of mitochondrial DNA content in adipose tissue of HIV–1–infected patients treated with NRTIS," *Antiviral Therapy,* 5(Suppl. 5):5 (abstract No. O6) (2000).

Carr, Andrew ; Miller, John; Law, Matthew ; Cooper, David A., A syndrome of lipoatrophy, lactic acidaemia and liver dysfunction associated with HIV nucleoside analogue therapy: contribution to protease inhibitor–related lipodystrophy syndrome, AIDS. 14(3):F25–F32, Feb. 18, 2000.

Moyla, Graeme, Mitochondrial toxicity hypothesis for lipoatrophy: a refutation [Research Letters], AIDS: vol. 15(3), pp. 413–415, Feb. 16, 2001.

Venhoff N, Walker UA., Mitochondrial disease in the offspring as a result of antiretroviral therapy, Expert Opin Drug Saf, vol. 5(3), pp. 373–381, May 2006.

* cited by examiner

*Primary Examiner*—Evelyn Huang

(57) ABSTRACT

The invention relates to the use of active ingredients, which increase the concentration of pyrimidine-based elements for nucleic acid biosynthesis in the body, in particular to the use of pyrimidine nucleosides and/or prodrugs produced therefrom, for reducing the side-effects of inhibitors of nucleic acid biosynthesis or their precursors, in particular by activating the biosynthesis of mitochondrial DNA (mtDNA). The invention also relates to the use of said active ingredients, in particular pyrimidine nucleosides and/or prodrugs for producing pharmaceutical preparations for reducing the aforementioned side-effects and to combinations or products for administering active ingredients of this type, in particular pyrimidine nucleosides and/or prodrugs produced therefrom, comprising inhibitors of nucleic acid biosynthesis or their precursors. The invention further relates to methods for treating the side-effects of inhibitors of nucleic acid biosynthesis or their precursors using the aforementioned active ingredients, in particular pyrimidine nucleosides and/or prodrugs produced therefrom, or the aforementioned combinations or products and to corresponding pharmaceutical preparations. Side-effects of HAART (Highly Active Anti-Retroviral Therapy) and side-effects of other anti-viral nucleoside analogous agents, which inhibits the mitochondrial γ-polymerases, can in particular be prophylactically and/or therapeutically treated in this manner.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *